(12) United States Patent
Utsunomiya et al.

(10) Patent No.: US 8,002,761 B2
(45) Date of Patent: Aug. 23, 2011

(54) DISPOSABLE DIAPER

(75) Inventors: Takeshi Utsunomiya, Shikokuchuo (JP); Keiji Torigoshi, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 393 days.

(21) Appl. No.: 12/225,839

(22) PCT Filed: Mar. 30, 2007

(86) PCT No.: PCT/JP2007/057280
§ 371 (c)(1),
(2), (4) Date: Sep. 30, 2008

(87) PCT Pub. No.: WO2007/114387
PCT Pub. Date: Oct. 11, 2007

(65) Prior Publication Data
US 2009/0069776 A1 Mar. 12, 2009

(30) Foreign Application Priority Data

Mar. 31, 2006 (JP) .................. 2006-101163
Mar. 31, 2006 (JP) .................. 2006-101165

(51) Int. Cl.
*A61F 13/15* (2006.01)
(52) U.S. Cl. ........ 604/391; 604/387; 604/389; 604/396; 604/392; 604/386
(58) Field of Classification Search .................. 604/391, 604/387, 389, 396, 392, 386
See application file for complete search history.

(56) References Cited

U.S. PATENT DOCUMENTS

| | | | |
|---|---|---|---|
| 3,694,867 A | 10/1972 | Stumpf | |
| 5,926,926 A | 7/1999 | Kato | |
| 6,142,986 A * | 11/2000 | Lord et al. | 604/391 |
| 2002/0022819 A1 | 2/2002 | Ronnberg et al. | |
| 2003/0119404 A1 | 6/2003 | Belau et al. | |
| 2004/0102745 A1 | 5/2004 | Linker, III et al. | |

FOREIGN PATENT DOCUMENTS

| | | |
|---|---|---|
| CA | 2 343 852 | 11/2001 |
| EP | 0 974 326 | 1/2000 |
| JP | 09-000317 | 1/1997 |
| JP | 11-335960 | 12/1999 |
| JP | 3490608 | 11/2003 |
| RU | 2 255 721 | 2/2004 |
| WO | WO 2007/001815 | 1/2007 |

* cited by examiner

*Primary Examiner* — Jacqueline F Stephens
(74) *Attorney, Agent, or Firm* — DLA Piper LLP (US)

(57) ABSTRACT

To improve the fastening property of a fastening type disposable diaper.
The problem is overcome by use of a disposable diaper having an engagement section that is constituted so that the separation strength off a fastening tape is constituted so as to decrease stepwise or continuously from a center portion in a width direction of a product toward edges on both sides or an engagement section made of a loop member sheet constituted so that loop elements of the loop base sheet may be exposed from holes 21*a*, 21*a* of a perforated cover sheet 21.

7 Claims, 8 Drawing Sheets

WIDTH DIRECTION

VERTICAL DIRECTION

DISPOSABLE DIAPER

TECHNICAL FIELD

The present invention relates to a disposable diaper, in particular, an open type disposable diaper that is worn by engaging fastening tapes disposed at edges on both sides of either a back side or a front side with an engagement section disposed between edges on both sides of a corresponding front side or back side to wear.

BACKGROUND ART

An open type disposable diaper is well known that includes a liquid pervious face sheet, a liquid impervious back sheet and an absorbent body disposed therebetween and is worn by fastening fastening tapes disposed at edges on both sides of a back side to a fastening portion disposed at a predetermined position on a front side is well known.

A disposable diaper of this kind adopts, as a fastening mechanism, a hook and loop fastener mechanism where an entirety or a part of a fastening tape is made into a hook member of a hook and loop fastener, at a predetermined position of a front side waist portion, over a width direction, a loop member sheet is bonded to form an engagement section, and the hook member is pressed and engaged with the loop member that is an engagement section to fasten.

Recently, another open type disposable diaper has also been known that adopts a hook and loop fastener mechanism called a target tape-less where, without forming an engagement section by bonding a loop sheet, an external surface side of a back sheet is formed of a nonwoven sheet and a front side waist portion of the back sheet is embossed over a width direction to render the back sheet itself an engagement section is also known.

A disposable diaper that adopts a hook and loop fastener mechanism like this, even after repetition of fastening and loosing at wearing, does hardly deteriorate in the engagement force and is fastened with appropriate shearing force to be excellent in wearing feeling.

On the other hand, in a disposable diaper that adopts a hook and loop fastener of the kind, it is general that, in order to respond to a movement of a wearer, the elasticity is imparted to a flap to which a fastening tape is bonded, the fastening tape per se is imparted with the elasticity, or an engagement section-forming region is provided with the elasticity to give the elasticity to a waist-encircling portion to form so that a wearer may move easily. Furthermore, without positively imparting the elasticity like this, owing to the elongation and the like of a constituting sheet material accompanying a movement of a wearer, a waist-encircling portion is expanded and contracted not a little.

However, an engagement section of an existing disposable diaper is formed so that the separation strength off a hook member does not vary depending on a region. Accordingly, when, for example, a fastening tape is engaged by pulling toward a center portion so as to wear slightly tight, the contraction force or the like of the fastening tape works stronger to be likely to come off. On the contrary, when a fastening tape is engaged with a position close to a side portion so as to wear slightly loose, the contraction force of the fastening tape does hardly work to result in engaging at unnecessary strength.

In the configuration, in order to keep an engagement state necessary and sufficient in a state where a waist-encircling portion is stretched, there remains only whether the separation strength between the fastening type and a loop member sheet and an embossed region, which constitute an engagement section, is constituted stronger or a fastening tape or a side flap is constituted stretchy to loosen the stretching force of a waist-encircling portion. However, in an aspect where the separation strength is made stronger, a fastening tape is difficult to repeat to fasten again to be less in advantage of a hook and loop fastener. On the contrary, when the stretching force of a waist-encircling portion is made weaker, front and back body parts tend to be displaced to cause leakage.

Furthermore, depending on, for example, a shape of a waist-encircling portion due to age of a wearer or frequent movements such as rolling-over or the like, the front and back body parts frequently cause displacement. At that time, the fastening tape is frequently peeled toward a product length direction. Accordingly, at that time, a displacement width of the front and back body parts is larger in edges on both sides in a width direction than in a center portion in a width direction of a product, accordingly, one where edges on both sides in a width direction are more difficult to peel than a center portion in a width direction of a product is desired.

Now, a hook and loop fastener is an engagement member where a loop member sheet having loop elements obtained by forming a fiber in loop or in arch and a hook member sheet having a napped hook element having a swelling head shape such as a hook shape or a mushroom shape that engages with the loop elements are pressed and engaged to allow exerting adhesive force. The hook and loop fastener is, being easy to fasten and loose and having appropriate engagement force, as mentioned above, as a fastening member or the like of a disposable diaper and the like, used in a variety of fields.

Conventionally, the loop member sheet of the hook and loop fastener has been formed by enhancing loops and the like by making use of needle punch, spun bond, spun lace or thermal contraction to a nonwoven fabric that uses a fiber of a synthetic resin such as nylon, polyester or the like.

In a loop member sheet containing such a synthetic resin fiber, in order to control the engagement force and to inhibit fibers from napping, by passing through a heated pattern roll or an embossing roll, a loop element is partially fused.

However, a loop member sheet where a loop element is partially fused to control the engagement force like this is hardened in a fused portion. Accordingly, when the loop sheet like this is used in an article that comes into contact with skin such as a disposable diaper, there is unfavorable stiff feeling. Furthermore, since a heat source is necessary to produce, much energy is consumed to be high in the production cost.

Furthermore, when a design is altered, a roll pattern has to be changed, accordingly, a design change is disadvantageously difficult to apply.

Still furthermore, when a fusing treatment is once applied, the engagement force is not restored thereafter, accordingly, it is impossible to design so that the engagement force may be restrained only when it is unnecessary to engage.

Patent Document 1: Japanese Patent Application Laid-Open (JP-A) No. 3490608
Patent Document 2: JP-A No. 09-317

DISCLOSURE OF THE INVENTION

In this connection, the present invention intends to provide 1) an open type disposable diaper that may be engaged always at suitable strength wherever a fastening position of a fastening tape may be to an engagement section, 2) a disposable diaper provided with a hook and loop fastener, in which, without necessitating fusing a fiber due to heat and without partially hardening, the engagement force can be controlled, a design change can be readily applied, and the engagement force can be restrained only at the time of being unnecessary and 3) in a target tape-less disposable diaper in particular, a disposable diaper of which engagement force is improved without accompanying a large design change of a back sheet and a fastening tape.

The present invention to solve the above problems will be described below.

<Invention of Claim 1>

An open type disposable diaper that includes: a liquid pervious face sheet; a liquid impervious back sheet; and an absorbent body disposed therebetween, wherein fastening tapes are disposed at edges of both sides of either one of a back side or a front side, the fastening tape is partially or entirely formed of a hook member of a hook and loop fastener, and the hook member is engaged with an engagement section disposed between edges of both sides of a front side or a back side for wearing, characterized in that the engagement section is disposed so as to extend from a center in a width direction of a product toward edges on both sides and the separation strength off the hook member is constituted so as to be different stepwise or continuously from a center portion in a width direction of a product towards edges on both sides and/or from one edge in a vertical direction of a product towards the other edge.

(Operation and Effect)

When the engagement section is disposed so as to extend from a center in a width direction of a product toward edges on both sides, the engagement section is formed wide for the front and back sides of a wearer, accordingly, an engagement operation is easy.

Furthermore, out of a region where a hook member is engaged in the engagement section, it is a center portion in a width direction, which is usually located at a farthest position and, at which an engagement state is easily and involuntarily cancelled due to pull toward edges on both sides of the fastening tape under influence of extension of a waist-encircling portion after engagement or movement of a wearer and under influence of a body shape of a wearer.

On the other hand, at edges on both sides, in a usual state, the engagement state is not so frequently cancelled involuntarily due to the pulling like this. However, depending on a movement of a wearer, front and back body parts are frequently displaced, accordingly, in a aspect where such a situation occurs frequently, the engagement state tends to be cancelled more in the edges on both sides in a width direction than in a center portion in a width direction of a product.

Accordingly, in the present invention, the engagement section may be constituted so that the separation strength off the hook member may be different stepwise or continuously from a center portion in a width direction of a product toward edges on both sides. That is, the separation strength may be set so as to decrease or increase stepwise or continuously from a center portion in a width direction toward edges on both sides.

Whether the separation strength is set so as to increase or decrease may be designed depending on an age or wearing aspect of an assumed wearer. For instance, if it is a product for a period where a movement is slight like a baby, the separation strength may well be made lower from a center portion toward edges on both sides in a width direction so that a center portion in a width direction of a product, in which the engagement state is most likely to be cancelled due to extension of a waist-encircling portion or the like, may be tightly engaged and edges on both sides, without unnecessarily strongly engaged, may well be readily stuck or peeled. For instance, if it is a product for an infant, by contrast, the separation strength may well be made higher from a center portion toward edges on both sides in a width direction.

When the separation strength is made lower or higher towards edges on both sides, the separation strength may be lowered stepwise for every certain range or continuously.

Furthermore, the engagement section of the present invention may be constituted so that the separation strength off the loop member may be differentiated stepwise or continuously from one edge in a vertical direction toward the other edge of the product.

The partial difference in the magnitude of the separation strength may be appropriately designed depending on an age of an assumed wearer or a wearing aspect. For instance, when a product is for an infant whose upper waist portion (navel periphery) largely throws out, it may be well that the separation strength is made higher from a center portion towards an upper side in a vertical direction to be tightly engaged in the proximity of an edge of a waist-encircling opening where the engagement state is most likely to be cancelled due to abdominal pressure and, in a lower waist portion, without unnecessarily strongly engaging, engagement and disengagement may be readily carried out. When it is a product for a grown man whose lower waist portion largely protrudes, on the contrary, the separation strength may well be made higher from a center portion toward a lower side in a vertical direction.

Furthermore, in the engagement section of the present invention, differences of the separation strengths in the width direction and the vertical direction may be combined. For instance, in a product for a baby, the separation strength between the engagement section and loop member may be made higher from a center portion in a width direction toward edges on both sides and from a center portion toward an upper side in a vertical direction.

The disposable diaper wherein an engagement section is formed by bonding a loop member sheet of a hook and loop fastener where many loop elements are formed to a back sheet.

(Operation and Effect)

Without changing a configuration of a diaper body, by appropriately designing a loop member sheet, an engagement section where engagement force is partially different can be formed.

The disposable diaper wherein a back sheet per se is partially formed into an engagement section.

(Operation and Effect)

In the present invention, a back sheet per se may be partially formed into an engagement section. For instance, when the outermost layer of the back sheet is made of a nonwoven fabric, by forming a loop element with a part of which the hook member is engaged, an engagement section is formed. This is an aspect so-called as target tape-less. As a process of forming an engagement section, an appropriate process such as an embossing process, a corrugating process or a process of napping with a pin may be adopted.

Now, when the embossing process is adopted, by differentiating depth or density of the embossing, the separation strength can be readily differentiated. For instance, when the embossing is applied, the loop element is crushed. Depending on an extent of the crushing, the separation strength varies. The deeper or denser the embossing is applied, the more the loop element is crushed, resulting in decreased separation strength of that portion. Accordingly, in the case of the target tape-less where an exterior face of a back sheet is formed of a fiber sheet such as a nonwoven sheet or the like, by embossing more rough or more deeply in depth from a center portion toward edges on both sides, the separation strength may be differentiated.

The disposable diaper wherein depending on difference between the densities or heights of the loop elements, the separation strength off the hook member is constituted so as to be different.

(Operation and Effect)

The engagement section is readily configured where the separation strength off the hook member is partially different. Here, the loop element is a loop or arch of a fiber formed on an engagement face of the loop member. In the loop and hook fastener, it goes without saying that the loop or arch is engaged with a napped hook element of the hook member having a swelling head such as a hook shape or mushroom shape for bonding the both elements.

The disposable diaper wherein the loop member sheet or back sheet that forms an engagement section is embossed and the embossing pattern is a pattern arranged along a machine direction or a cross direction.

(Operation and Effect)

When an embossing pattern is arranged along a machine direction or a cross direction, the napping of fibers caused by peeling of the fastening tape is decreased. Here, the machine direction is an anteroposterior direction of a product and the cross direction is a product width direction.

The disposable diaper wherein the engagement section is;

a loop sheet having a configuration where, on a loop element-forming surface of a loop base sheet on which many loop elements are formed, a perforated cover sheet having a plurality of holes is stacked and bonded to engage with a hook member through a loop element-forming surface exposed from the holes of the perforated cover sheet or a portion that is configured so that a range containing a loop member on which many loop elements formed by a fiber of a back sheet per se are formed is covered with a perforated cover sheet having a plurality of holes and, through the loop element-forming surface exposed from the holes, is engaged with the hook member.

(Operation and Effect)

In the present invention, the engagement force is very easily controlled only by varying size, number and pattern of the holes of the perforated cover sheet. Furthermore, since the loop base sheet having loop elements or loop base portion is not fused, there is hardly a hardened portion over a wide range for controlling the engagement force. Still furthermore, heat energy as well is not required so much.

In particular, when the loop base sheet is a nonwoven fabric, since the loop sheet is made cheaply, the cost can be reduced.

<Invention of Claim 2>

The disposable diaper according to claim 1 wherein the perforated cover sheet is bonded, through a hot-melt adhesive, to a loop base sheet or a back sheet.

(Operation and Effect)

By use of a hot-melt adhesive, without a hardened portion, the both sheets can be bonded.

<Invention of Claim 3>

The disposable diaper according to claim 1 or 2 wherein the perforated cover sheet has the elasticity and is partially bonded to the loop base sheet or the back sheet and the respective holes are constituted scalably due to expansion and contraction of the perforated cover sheet.

(Operation and Effect)

In the present invention, the holes are constituted scalably due to the elasticity of the perforated cover sheet. Accordingly, the cover sheet may be elongated during usage to engage with the hook member in a state where the holes are expanded and, when the engagement is unnecessary, as a state where the perforated cover sheet is contracted, the holes are made smaller to make an exposed portion less. Thereby, the engagement force is restrained during unnecessary time and the engagement force is exerted during necessary time. Particularly, it is preferable that the perforated cover sheet has the elasticity with resilience.

<Invention of Claim 4>

The disposable diaper according to any one of claims 1 through 3 wherein between the perforated cover sheet and the loop base sheet or between the perforated cover sheet and the back sheet, an elastic material with resilience is disposed.

(Operation and Effect)

In the present invention, between the loop base sheet or the like and the perforated cover sheet, an elastic material with resilience is disposed. Accordingly, when the elastic material is contracted, the loop base sheet or the like is contracted to cause wrinkles to hide holes between wrinkles, and, when the elastic material is stretched, the holes are made so as to be exposed from between the wrinkles. Accordingly, it is possible to constitute so that, after a hook member is engaged in a state where the holes are exposed during stretching, an elongation of the hook member or the like is cancelled to again hide holes unnecessary for engagement between the wrinkles.

<Invention of Claim 5>

The disposable diaper according to any one of claims 1 through 4 wherein the perforated cover sheet is provided with many loop elements for engaging with the hook member formed on an external surface side of the diaper.

(Operation and Effect)

Both of a loop element-forming surface exposed from the holes of the perforated cover sheet and the loop elements of the perforated cover sheet per se are engaged with a hook member, accordingly, the engagement force is enhanced as a whole. The magnitude of the engagement force is controlled by a formation rate of the holes. When a material of the loop base sheet covered with the perforated cover sheet and a material of the perforated cover sheet are different in separation strengths, the engagement force can be more effectively controlled.

<Invention of Claim 6>

The disposable diaper according to any one of claims 2 through 5 wherein in at least one of predetermined ranges set as an engagement region of the loop member sheet, the loop base sheet, the perforated cover sheet and the back sheet, all of which have loop elements, many penetrating openings are disposed.

(Operation and Effect)

The hook member of the fastening tape is engaged with many openings, accordingly, the engagement force can be enhanced. In particular, even with a less-bulky nonwoven fabric having small basis weight, sufficient engagement force may be imparted. The engagement force with the fastening tape can be controlled by a formation rate of the openings.

<Invention of Claim 7>

The disposable diaper according to claim 6 wherein the openings are formed by applying an opening operation from a side of a surface that is an internal surface side of a diaper toward a side of a surface that is an external surface side of diaper and an opening edge stands up outwardly.

(Operation and Effect)

Since the opening edge stands up outwardly even a little, the hook elements become easy to engage, thereby, the engagement force becomes easy to exert.

Effect of the Invention

As detailed above, according to the present invention, an open type disposable diaper can be provided wherein, any portion of the engagement section is used for fastening, it is always possible that an engagement state has favorable strength, particularly in a center portion, where the engagement is likely to be cancelled under influence of extension of a waist-encircling portion, can be firmly engaged, while in edges on both sides, which are less in the risk of canceling, are not excessively strongly engaged.

Furthermore, a disposable diaper provided with a hook and loop fastener mechanism can be provided, wherein, without necessitating fusing a fiber due to heat and without partially hardening, the engagement force can be controlled, a design change can be readily applied and the engagement force can be restrained only during an unnecessary time.

Herein, in the present invention or specification, as far as a measurement method is not varied at measuring the respective portions of the engagement section, a measurement method of separation strength is not particularly restricted. In short, a measurement method is enough to be able to measure force when a hook member and a loop member are peeled after their bonding. A particularly preferable measurement method of the separation strength will be described later.

Furthermore, in the specification, easiness in canceling the engagement of a fastening tape off an engagement section in a wearing state is sometimes referred as the engagement force.

BEST MODE FOR CARRYING OUT THE INVENTION

In the next place, embodiments of the present invention will be detailed with reference to the drawings.

First Embodiment

FIG. 1 shows a fastening disposable diaper Z1 according to a first embodiment of the present invention. The disposable diaper Z includes a liquid pervious face sheet 11 located on a skin side of a user, a liquid impervious back sheet 12 that is located on an external side of a product and substantially liquid impervious, and an absorbent body 13 that is disposed therebetween, has a rectangular shape or preferably a sand clock shape and has a certain extent of stiffness, wherein, on edges on both sides of a back side, fastening tapes Y1 and Y2 for fastening are disposed.

The fastening tapes Y1 and Y2 are formed of, except for portions bonded to edges on both sides and tip portions that are tab parts, a hook member of a hook and loop fastener and an engagement section X1 with which the hook member is engaged is disposed to an external front side of the back sheet 12.

The back sheet 12 forms a substantial rectangle that is wider than the absorbent body 13 and provided with, at a substantial center portion in a longitudinal direction, leg-encircling portions formed by cutting edges on both sides in arch and is formed by laminating an external nonwoven sheet 12B for improving the texture on an external surface of a liquid impervious film sheet 12A such as a polyethylene film or the like, followed by pressing and bonding by means of an embossing process or the like applied through a hot-melt adhesive. The external nonwoven sheet 12B is constituted to have dense fiber loops or dense fiber arches so as not to engage with the hook member. In the embodiment, the nonwoven sheet is not necessarily disposed, that is, the back sheet may be formed only of a liquid impervious film sheet.

Herein, the back sheet 12 is desirably constituted so as to have the moisture penetration in the range of 0.5 to 4.0 g/100 cm 2 hr, and, the liquid impervious film sheet 12A and the nonwoven sheet 12B are desirably bonded so as to have the separation strength in the range of 115 to 135 g/25 mm. The separation strength is the 180° separation strength when, under conditions of 25° C. and 65% RH, a back sheet 12 is sampled at a width of 25 mm in a width direction (level direction) of an original fabric and at a length of 100 mm, followed by peeling from one end at a speed of 300 mm/min.

As the liquid impervious film sheet 12A used in the back sheet 12, a known liquid impervious film sheet that is used as a back sheet 12 of an absorbent article can be used without particular restriction. Specific examples thereof include various kinds of synthetic resinous sheets such as a polyethylene sheet, a polypropylene sheet, a polyurethane sheet, a polyethylene terephthalate sheet or the like and porous synthetic resin sheets obtained by disposing many fine vent holes to impart the air permeability to the synthetic resinous sheets. A thickness and the stiffness of the liquid impervious film sheet may be appropriately selected according to known criteria, considering the thickness and stiffness of the nonwoven sheet to be laminated.

As the nonwoven sheet used in the back sheet 12, known nonwoven sheets used as the back sheet of an absorbent article can be used. Examples thereof include nonwoven fabric formed by appropriately processing a web made of synthetic resin such as olefin including polyethylene, polypropylene and the like, polyester, polyamide and the like; recycled fiber including rayon, cupra and the like; and natural fiber including cotton and the like. They are manufactured by an appropriate process such as a spun lace process, a spun bond process, a thermal bond process, a melt blown process, a needle punch process, a thermal contraction process and the like.

Out of the processing methods, the spun lace process is excellent in flexibility and drape property and the thermal bond process is superior in bulkiness and softness, accordingly, these may be appropriately selected depending on the object. Herein, the nonwoven sheet may be a laminated nonwoven sheet. For instance, a nonwoven laminate obtained by appropriately laminating two or more layers of a spun bond nonwoven fabric (S) layer where a web is formed by means of a spun bond process; and a melt blown nonwoven fabric layer (M) where a web is formed according to a melt blown process may be used as a raw material.

On the other hand, an engagement section X1 is formed by bonding a general loop sheet to a back sheet 12 with a hot-melt adhesive. The engagement section X1 is disposed, in a product front side, extending from a center in a product width direction toward edges on both sides. In an illustrated example, the engagement section is formed in a horizontally long rectangle as a desirable form, however, it is not particularly restricted to the rectangle. Other shapes may be adopted. As a bonding method to the back sheet 12, an appropriate known method corresponding to a loop member being used may well be used.

Herein, the engagement section X1 of the embodiment is characterized by configuring so that the separation strength between the fastening tapes Y1 and Y2 and the hook member may vary stepwise from a center portion in a width direction of a product toward edges on both sides. In an illustrated example, the engagement section X1 is divided into 5 zones and, as the relationship between the zone and the separation strength is shown in FIG. 2, the separation strength is constituted so that the zone D1 located in the center may be highest, and, in the order of the zone D2 adjacent thereto and the zone D3 adjacent further thereto, the separation strength may be decreased. The specific separation strengths of the respective zones may be appropriately determined, and basically, it is desirable that the separation strength is divided stepwise with difference substantially in the range of 100 to 1500 gf, particularly 140 to 400 gf. When the separation strength is less than 100 gf, sufficient engagement is not obtained, and, when the separation strength exceeds 1500 kgf, since the engagement force is excessively strong, at engagement and disengagement, the engagement section tends to be napped.

The measurement method of the separation strength is carried out as shown below. In the beginning, a cloth tape having width 50 mm×length 100 mm is folded into two in a width direction to form a two-folded cloth tape having width 25 mm×100 mm, and to one end of the cloth tape, a fastening tape is firmly bonded. At that time, the hook member of the fastening tape is set so as to locate outside of a tip of the cloth tape.

On the other hand, to a stainless planar plate, the loop member according to the present invention is bonded by use of a double-sided adhesive tape with a loop element-forming surface kept as a top surface. Furthermore, both edges are fixed with a Kraft tape.

In the next place, after the hook member and the loop element-forming surface are brought into contact, a roller having a weight of 2 kg is once reciprocated over them from a cloth tape side to press and attach the fastening tape and the loop sheet. Furthermore, at the other end of a side opposite to a side where a fastening tape of a cloth tape is bonded, a copper weight of 1 kg is hanged for 10 sec to apply the shearing force to a pressed and attached portion to secure the engagement.

Thereafter, the stainless planar plate and the other end on a side opposite to a side where the fastening tape of the cloth tape is bonded are gripped by a jig of a tensile testing machine. At that time, a tensile direction of the jig that grips the other end on a side opposite to a side where the fastening tape of the cloth tape is bonded is set at 90° to the stainless planar plate.

Thus, after the jig is set to a tensile testing machine so that a final peel angle may be 90°, a pressed and attached portion is peeled at 300 mm/min, and a weighted average of high and low values measured on this occasion is taken as the separation strength. The measurement value is represented by the average of 3 to 10 effective measurement values. Furthermore, at the measurement, a sample is set so as to carry out a measurement in a cross direction versus cross direction. Still furthermore, as to the size of the test piece, a hook member is set to 47 mm±3 mm (machine direction)×93 mm (cross direction) and a loop base sheet is set to 23.5±1.5 mm (machine direction)×24 mm (cross direction). Herein, the machine direction is an anteroposterior direction of a product and a cross direction is a width direction of the product.

When the separation strength is tested, a tensile testing machine (trade name: AOUTGRAPH AGS-G100N, produced by Shimadzu Corporation) may be used.

On the other hand, the number of zones of the engagement section, without restricting to 5 zones as illustrated, may be 3 zones or 5 zones or more. However, as far as the separation strength is set so as to decrease stepwise, a zone desirably has a size where the hook member formed on the fastening tape can be fitted.

In the embodiment, between zones located line symmetrically with respect to a center line in a width direction of a product, the separation strengths are constituted so as to be identical. However, they are not necessarily identical.

Furthermore, like the relationship between the separation strength and the position of the engagement section shown in FIG. 3, without forming zones, the separation strength may be constituted so as to continuously decrease from a center portion in a width direction of a product toward edges on both sides.

Still furthermore, the engagement section X1 is, irrespective of the zones, desirably designed so that the shearing force with the hook member of the fastening tape may be 1 to 10 kg and preferably 3 to 8 kg. When the shearing force is less than 1 kg, the engagement is likely to be cancelled. On the other hand, when the shearing force exceeds 10 kg, the engagement is too strong.

The shearing force is measured as shown below. In the beginning, on the stainless planar plate, the loop sheet according to the present invention is bonded by use of a double-sided adhesive tape with a loop element-forming surface set as a top surface. Furthermore, both ends are fixed by use of a Kraft tape. At that time, in the periphery of the loop base sheet, a margin of the stainless planar plate is left.

Then, after the hook member of the fastening tape is brought into contact with the loop element-forming surface, thereon, a roller having weight of 2 kg is reciprocated once from the cloth tape side to press and attach the hook member and the loop base sheet.

Thereafter, the margin portion of the stainless planar plate and one end of the fastening tape are gripped by a jig of the tensile testing machine. At that time, a distance between grips is set at 50 mm. After the chucking comes to completion, the jig is pulled in a shearing direction of the hook member and the loop base sheet at a tensile speed of 30 mm/min to measure the maximum shearing force. A measurement value is represented by the average of 3 to 10 effective measurements. Furthermore, at the measurement, a sample is set so as to carry out a measurement in a cross direction versus cross direction. Still furthermore, as to the size of the test piece, a hook member is set to 47 mm±3 mm (machine direction)×93 mm (cross direction) and a loop base sheet is set to 23.5±1.5 mm (machine direction)×24 mm (cross direction). Herein, the machine direction is an anteroposterior direction of a product and a cross direction is a width direction of the product.

On the other hand, a loop member of a hook and loop fastener that constitutes an engagement section X1 is constituted of a sheet-like material provided with loop elements suitable for engagement with the hook members disposed to fastening tapes Y1 and Y2. Known various kinds of loop base sheets in the existing examples may be used by appropriately applying processing or the like.

As a loop sheet, there can be listed a woven fabric on one surface of which many loop- or arch-shaped loop elements are formed, a nonwoven fabric on one surface of which many loop- or arch-shaped loop elements are conspicuously formed by applying an appropriate processing method such as a spun lace process or the like to a web made of a synthetic fiber, a recycled fiber, a natural fiber such as cotton or the like and a sheet obtained by bonding the above nonwoven fabric to a base sheet.

Herein, when, as mentioned above, the separation strength is differentiated stepwise or continuously between zones of the engagement section X1, for example, a loop member can be applied in which the density of the loop elements in each zone is differentiated. Alternatively, such differentiating can be attained by e.g., embossing one loop sheet at every zone so as to appropriately crush the loop elements.

On the other hand, a hook member of a hook and loop fastener that constitutes a part or an entirety of fastening tapes Y1 and Y2 is constituted of a hook sheet having napped hook elements such as hook-shaped or mushroom-shaped swelling heads that engage with loop elements of the loop member that is used in the engagement section. As a method of producing a fastening tape from the hook sheet, a known method may be used without restriction. Furthermore, sizes and density of the napped hook elements such as hook-shaped or mushroom-shaped swelling heads as well may well be appropriately selected in such range that appropriate separation strength can be obtained in association with the loop member.

On the other hand, though not shown in the drawing, the disposable diaper Z1 of the embodiment, with many elastic rubber threads with resilience disposed extended between the fastening tapes, is constituted so as to extend or contract between the fastening tapes Y1 and Y2 on a back side. Thereby, a fastening acceptable zone of the fastening tapes Y1 and Y2 at the time of fastening is expanded and thereby a fastening acceptable zone due to difference of body shapes of wearers is expanded. Furthermore, owing to such extension and contraction, the fitting feeling at the time of wearing is improved.

Alternatively, for expanding and contacting the disposable diaper between the fastening tapes Y1 and Y2 on a back side, the rubber threads are not adopted, and a configuration is adopted instead where, between tip portion of each fastening tape Y1, Y2 and its base end portion, an appropriate elastic member such as an elastomer sheet or the like is interposed and, on a tip end side with respect to the interposed elastic member, a hook member of a hook and loop fastener is disposed to expand and contract the fastening tape Y1, Y2 per se may be adopted.

Furthermore, a configuration may be adopted as well where, between a so-called side flap portion to which the fastening tape Y1, Y2 is bonded and another portion, an elastic member such as an elastomer sheet or the like is interposed to allow expanding and contracting between the fastening tapes Y1 and Y2 on a back side.

Also in these cases, the fitting feeling and the acceptable range for the difference of body type are improved.

The stretching forces of the rubber thread and the elastic member can be designed without problems within a range adopted by a known disposable diaper.

On the other hand, in the embodiment, the face sheet 11 has a shape identical with that of the back sheet 12, extends outwardly beyond the edge portion of the absorbent body 13 and is bonded to the back sheet 12 with a hot-melt adhesive or the like. As the face sheet 11, other than various kinds of nonwoven fabrics such as a spun bond nonwoven fabric, an air through nonwoven fabric, a SMS nonwoven fabric, a point bond nonwoven fabric or the like, within a range where the liquid permeability may be secured, a plastic film such as polyethylene film or the like and a laminated nonwoven fabric obtained by laminating a plastic film and a nonwoven fabric as well are used. Furthermore, a net-like material obtained by flat-weaving threads of nylon, polyethylene terephthalate or the like may be used as well.

The absorbent body 13 is formed by a fiber aggregate, which is made of fiber accumulating pulp or tow, which includes an absorbent polymer and which is covered with a pulp sheet or the like. As a fiber of the fiber aggregate (hereinafter, simply referred to as a constituent fiber of tow), there can be listed polysaccharides or derivatives thereof (such as cellulose, cellulose ester, chitin, xanthone and the like), synthetic polymers (such as polyethylene, polypropylene, polyamide, polyester, polylactamide, polyvinyl acetate and the like) and the like. Out of them, cellulose ester and cellulose are particularly preferred.

Preferable examples of the super absorbent polymers include carboxy methyl cellulose, polyacrylic acid and salts thereof, crosslinked products of acrylate polymers, starch-acrylic acid graft copolymers, hydrolyzed products of starch-acrylonitrile graft copolymers, crosslinked products of polyoxy ethylene, crosslinked products of carboxy methyl cellulose, polyethylene oxide, partially crosslinked products of water-swelling polymers such as polyacrylamide or the like, copolymers of isobutylene and maleic acid and the like. To each of the super absorbent polymers, a blocking inhibitor can be added to restrict the blocking property caused by moisture absorption of a product. Each of such super absorbent polymers include has various shapes such as powder shape, particulate shape, granule shape, pellet shape, sol shape, suspension shape, gel shape, film shape, nonwoven fabric shape and the like. All these shapes are usable in the present invention and particulate-shape is preferable.

The absorbent article in the present invention is not restricted to the above configuration of this embodiment. For instance, a configuration may be adopted where elastic members with resilience such as rubber threads or the like commonly used in a disposable diaper or the like are disposed at various parts in an absorbent articel. Another configuration may be used as well in which a second sheet is disposed between a face sheet and an absorbent body of an absorbent article to diffuse a body fluid or the like.

Second Embodiment

In the first embodiment, as an engagement section X1 of fastening tapes Y1 and Y2, a loop sheet is bonded to a back sheet. However, a second embodiment is a mode so-called target tape-less where, not bonding a loop sheet to a back sheet, but an external face of a back sheet 12 per se is partially appropriately embossed to form a loop member to use this as an engagement section X1. A disposable diaper Z2 according to the second embodiment is shown in FIG. 4. In what follows, the second embodiment will be explained by mainly describing different points from the first embodiment.

The back sheet 12 according to the first embodiment does not necessarily require disposing an external nonwoven sheet 12B. However, in the second embodiment, in order to improve texture and to form an engagement section, a nonwoven sheet 12B or a woven sheet is always disposed on an external surface side.

For bonding the nonwoven sheet 12B and a liquid impervious film sheet 12A, pressing and attaching is carried out by means of an embossing process or the like through a hot-melt adhesive.

A basis weight of the nonwoven sheet 12B is preferably from 10 to 100 g/m$^2$ and more preferably from 20 to 60 g/m$^2$. When the basis weight of the nonwoven fabric is less than 10 g/m$^2$, a space where a hook member is engaged is not sufficiently maintained and, when the fastening tape is peeled, the nonwoven sheet is broken. On the other hand, when the basis weight exceeds 100 g/m$^2$, the productivity of the nonwoven fabric is deteriorated and the fastening of the fastening tape to a portion other than the engagement section becomes unfavorably conspicuous.

On the other hand, in the back sheet 12 of the embodiment, in a range containing a range where an engagement section X1 is formed, between an external nonwoven sheet 12B and a liquid impervious film sheet 12A, an intermediate nonwoven sheet 12C is disposed. When the intermediate nonwoven sheet 12C is interposed, the corresponding portion becomes bulky to be excellent in the intrusion feeling when the fastening tapes Y1 and Y2 are pressed and bonded to the engagement section X1, and, the delamination strength is improved to inhibit the external nonwoven sheet 12B from delaminating when the fastening tapes Y1 and Y2 are stuck or peeled.

Herein, the liquid impervious film sheet 12A and the nonwoven sheet 12B in an interposing section of the intermediate nonwoven sheet 12C are desirably bonded so that the separation strength may be 175 to 195 g/25 mm. The separation strength is 180° separation strength when, under conditions of 25° C. and 65% RH, a back sheet 12 is sampled at a width of 25 mm in a width direction (level direction) of an original fabric and at a length of 100 mm, followed by peeling from one end at a speed of 300 mm/min.

When an embossing process is adopted to form an engagement section X1, embossing is applied according to a known process. For instance, after a back sheet 12 is produced, to an embossing machine provided with a convex embossing roll on a predetermined position of which an embossing convex pattern is formed and a rubber roll provided with the flexibility to an extent by which a convex portion of the convex embossing roll facing thereto is fitted into, the back sheet may well be supplied so that a nonwoven sheet side may be a convex embossing roll side to emboss.

Furthermore, an embossing machine provided with a concave embossing roll on which a concave portion corresponding to a convex portion of the convex embossing roll is formed may be used.

The engagement section X1 of the embodiment as well is provided with 5 zones different in the separation strength similarly to the first embodiment. The difference in the separation strength between the zones is differentiated according to the embossing density. The embossing depth as well may be used to differentiate.

What degree of the embossing depth or embossing density is specifically adopted depends on the basis weight of the nonwoven sheet and a configuration of the hook member. An appropriate design may be applied. Herein, as an embossing pattern imparted as an engagement section, a known pattern commonly applied to this target tape-less type may be adopted, and a pattern is preferable where emboss is arranged along a machine direction or a cross direction determined when the back sheet is formed. In this pattern, usually, emboss is disposed along a longitudinal direction or a width direction determined when a product is formed, and, thereby, such product can be obtained that is less in napping which would be caused by engagement and disengagement of the fastening tape.

Though not shown in the drawing in particular, when an emboss is disposed along a longitudinal direction of a product, the elasticity and air permeability of the waist-encircling portion are excellent. Herein, in the present invention, disposing along a longitudinal direction of a product is not necessarily restricted to a straight line emboss, that is, even the emboss that is formed zigzag in a longitudinal direction side of a product is included. Furthermore, though not shown in the drawing, an embossing pattern of an ellipse of which major axis direction runs along a longitudinal direction of a product is also included. There is no problem as far as a longitudinal direction of the emboss runs along a longitudinal direction of a product.

Third Embodiment

A disposable diaper Z3 according to a third embodiment is shown in FIG. 5. In the disposable diaper Z3 according to the third embodiment, an engagement section X1 is formed from an aggregate of a plurality of engagement units x, x . . . . The engagement units x, x . . . are formed by miniaturizing a loop sheet of a hook and loop fastener. The engagement section is formed of 5 zones different in sizes of the engagement units x, x . . . . In a zone D1 located in the center, the largest engagement units are used and thereby the separation strength is set highest, the sizes of the engagement units used in a zone D2 adjacent to the D1 and a zone D3 adjacent to the D2, respectively, are set smaller in this order, and thereby, the engagement section is constituted so that the separation strength may decrease toward edges on both sides. The engagement section may be constituted so that the sizes of the engagement units x, x . . . are set same in each of the zones and due to the difference of disposition density the separation strength with the hook member in the respective zones may be differentiated. Other configurations are same as that of the first embodiment.

Fourth Embodiment

In the next place, a disposable diaper of a fourth embodiment will be described. In a disposable diaper Z4 of the fourth embodiment, a loop member sheet used as an engagement section in the first embodiment is constituted by use of a loop member sheet for a hook and loop fastener characteristic in by easy control of the engagement force.

The loop member sheet of the characteristic hook and loop fastener is utilized in, other than the disposable diapers of the embodiment, disposable products such as absorbent articles, surgical coats, packing materials or the like, without restricting to the disposable diapers.

Configurations other than the characteristic engagement section are same as that of the first embodiment. Accordingly, in what follows, the loop member sheet, which is used as the characteristic engagement section and which is different from the first embodiment, will be mainly described.

In a loop member sheet X2 of a hook and loop fastener according to the embodiment, as shown in FIGS. 6 and 7, on a loop element 20a forming surface of a loop base sheet 20 on which many loop elements 20a, 20a . . . of which fibers are formed into loop or arch, a perforated cover sheet 21 having a plurality of holes 21a, 21a . . . is laminated and bonded with an adhesive 22, and from the holes 21a of the perforated cover sheet 21, a part of a surface where many loop elements 20a, 20a are formed is externally exposed.

In the loop member sheet, when an arrangement mode of the holes 21 disposed on the perforated cover sheet is appropriately designed to control an exposed area of the loop elements, the engagement force to a part or whole of a hook member of the engagement section is controlled very readily. That is, when a perforated cover sheet has a uniform arrangement mode of holes, the total engagement force of the engagement section is readily controlled. On the other hand, when a perforated cover sheet has a non-uniform arrangement mode of the holes, the part of the engagement force of the engagement section is readily controlled.

For instance, when a plurality of kinds of holes different in area are disposed in individual zones or the disposition densities of the holes of individual zones are differentiated, an engagement section different partially in the engagement force is conveniently formed. By carrying out thus, in comparison with a case where the loop elements of the loop base sheet are fused or crushed by embossing to partially control the engagement force, which advantageously prevents being hard of the engagement section.

Herein, the loop base sheet 20 is a sheet provided with many loop elements 20a, 20a suitable for engagement with a corresponding hook sheet and known various kinds of loop member sheets per se in existing examples may be used. For instance, there can be listed a woven fabric on one surface of which many loop-shaped or arch-shaped loop elements are formed or a nonwoven fabric obtained by processing a web made of a synthetic fiber such as olefin including polyethylene, polypropylene and the like, polyester, polyamide and the like, recycled fiber including rayon, cupra and the like and natural fiber such as cotton and the like. They are manufactured by an appropriate process such as a spun lace process, a spun bond process, a thermal bond process, a melt-blown process, a needle punch process, a thermal contraction process or the like to form loop-shaped or arch-shaped loop elements on one surface. From the viewpoint of enabling to produce less expensively, a nonwoven fabric is more preferred.

Among the processes by which loop-shaped or arch-shaped loop elements are conspicuously formed to a nonwoven fabric, the spun lace process is excellent in the flexibility and drape property and the thermal bond process is superior in being bulky and softness, accordingly, these may be appropriately selected depending on the object. Herein, the nonwoven fabric may be a laminated nonwoven fabric. For instance, there are can be listed a nonwoven fabric laminate obtained by appropriately laminating two or more layers of a spun bond nonwoven fabric (S) layer where a web is formed by means of a spun bond process; and a melt blown nonwoven fabric layer (M) where a web is formed according to a melt blown process may be used as a raw material.

When a loop base sheet 20 is designed, to what extent the separation strength between the loop base sheet 20 and the corresponding hook member is set may well be appropriately selected depending on the application. It goes without saying that it must not be a range where, without covering with the perforated cover sheet 21, the engagement force becomes insufficient. Furthermore, the separation strength where a perforated cover sheet 21 that is in an upper layer is damaged during peeling or fibers are pulled out of the holes 20a, 20a to be high in the risk of causing the napping is excessive in the application where engagement and disengagement are repeated. Furthermore, such separation strength is also excessive that too large range is covered with the perforated cover sheet 21 to restrain the engagement force thereby a substantial advantage is lost. For example, such case is excessive that 98% or more is covered in terms of area ratio.

In terms of specific numerical value, the separation strength is desirably designed so as to be from 100 to 1500 gf and preferably from 140 to 400 gf.

The measurement method of the separation strength is carried out as shown below. In the beginning, a cloth tape having width 50 mm×length 100 mm is folded into two in a width direction to form a two-folded cloth tape having width 25 mm×100 mm, and to one end of the cloth tape, a hook member sheet is firmly bonded. At that time, the hook member of the hook member sheet is set so as to locate outside of a tip of the cloth tape.

On the other hand, to a stainless planar plate, the loop base sheet according to the present invention is bonded by use of a double-sided adhesive tape with a loop element-forming surface set a top surface. Furthermore, both edges are fixed with a Kraft tape.

In the next place, after the hook member and the loop element-forming surface are brought into contact, a roller having a weight of 2 kg is reciprocated once over them from a cloth tape side to press and attach the hook sheet and the loop base sheet. Furthermore, at the other end of a side opposite to a side where a hook sheet of a cloth tape is bonded, a weight of 1 kg is hanged for 10 sec to apply the shearing force to a pressed and attached portion to secure the engagement.

Thereafter, the stainless planar plate and the other edge on a side opposite to a side where the hook member sheet of the cloth tape is bonded are gripped by a jig of a tensile testing machine. At that time, a tensile direction of the jig that grips the other edge on a side opposite to a side where the hook member sheet of the cloth tape is bonded is set so as to be 90° to the stainless planar plate.

Thus, after the jig is set to a tensile testing machine so that a final peel angle may be 90°, a pressed and attached portion is peeled at 300 mm/min, and an weighted average of high and low values measured at that time is taken as the separation strength. The measurement value is obtained by averaging effective measurement values of 3 to 10 times. Furthermore, at the measurement, a sample is set so as to carry out a measurement in a CD versus cross direction. Still furthermore, as to the size of the test piece, a hook member is set to 47 mm±3 mm (machine direction)×93 mm (cross direction) and a loop base sheet is set to 23.5±1.5 mm (machine direction)×24 mm (cross direction). Herein, the machine direction is an anteroposterior direction of a product and a cross direction is a width direction of the product.

When the separation strength is tested, a tensile testing machine (trade name: AOUTGRAPH AGS-G100N, produced by Shimadzu Corporation) may be used.

On the other hand, when the loop base sheet 20 is designed, to what extent the shearing force between the loop base sheet 20 and a corresponding hook member is set is appropriately selected as well depending on the application. The shearing force is not desirable that does not cause engagement even when the perforated cover sheet 21 is not used. Furthermore, the shearing force is neither desirable by which the load is applied to an inner periphery portion of the hole, possible causing damage. On the contrary, the shearing force is not desirable that is excessively strong in the engagement feeling to give hard feeling, resulting in losing advantages of the hook and loop fastener is not desirable.

In terms of specific numerical value, the shearing force is designed desirably so as to be 1 to 10 kg and preferably 3 to 8 kg. The shearing force is measured as shown below. In the beginning, on the stainless planar plate, the loop base sheet according to the present invention is bonded by use of a double-sided adhesive tape with a loop element-forming surface set a top surface. Then, both edges are fixed by use of a Kraft tape. At that time, in the periphery of the loop base sheet, a margin of the stainless planar plate is left.

Then, after the hook member of the fastening tape is brought into contact with the loop element-forming surface, thereon, a roller having weight of 2 kg is reciprocated once from the cloth tape side to press and attach the hook member and the loop base sheet.

Thereafter, the margin portion of the stainless planar plate and one end of the fastening tape are gripped by a jig of the tensile testing machine. At that time, a distance between grips is set at 50 mm. After the chucking comes to completion, the jig is pulled in a shearing direction of the hook member and the loop base sheet at a tensile speed of 30 mm/min to measure the maximum shearing force. A measurement value is obtained by averaging effective measurement values of 3 to 10 times. Furthermore, at the measurement, a sample is set so as to carry out a measurement in a cross direction versus cross direction. Still furthermore, as to the size of the test piece, a hook member is set to 47 mm±3 mm (machine direction)×93 mm (cross direction) and a loop base sheet is set to 23.5±1.5 mm (machine direction)×24 mm (cross direction). Herein, the machine direction is an anteroposterior direction of a product and a cross direction is a width direction of the product.

On the other hand, the perforated cover sheet 21 is used to cover the loop element-forming surface of the loop base sheet 20 to control the engagement force of the loop base sheet 20, accordingly, a sheet material smaller in the engagement force with the hook member than with the loop base sheet 20 may well be used.

However, the perforated cover sheet 21 is not restricted to a sheet that does not engage with the hook member. For instance, such sheet as well may be used that has loop elements capable of engaging with the hook member. A sheet material as well may be used that has the engagement force stronger with the hook member than that with the loop base sheet. These applications enlarge design variation of partial engagement force and separation strength with the hook member of the engagement section.

Raw materials of the perforated cover sheet 21 are not particularly limited and include various kinds of resinous film sheet such as a polyethylene film sheet and the like, a nonwoven sheet, a woven sheet, a flexible sheet and other various kinds of known sheet materials. When a perforated cover sheet that has loop elements is used, a sheet material different from the loop base sheet may well be selected.

When a nonwoven sheet is used as the perforated cover sheet, a basis weight of fiber is increased to heighten the fiber density or, by controlling a processing degree due to various kinds of processing methods such as a spun lace method or the like, the number or the loop height of loop-shaped portion or arch-shaped portion on a fiber surface is made less, thereby, a nonwoven sheet is formed that is smaller in the engagement force with the hook member than that with the loop base sheet 20.

As the perforated cover sheet 21, when the texture feeling is preferred, a nonwoven sheet is suitable, and, when the restraint of the engagement force is preferred, a resin film sheet high in the surface smoothness is suitable.

A plurality of holes 21a, 21a disposed to the perforated cover sheet 21 is exposing holes 21a, 21a for externally exposing loop elements 20a, 20a of the loop base sheet 20 and a hook member engages with the loop base sheet 20 via the holes 21a, 21a.

Accordingly, considering location of an engagement section in a diaper, area, number, location and the like of open regions of the holes 21a, 21a are appropriately designed so that the engagement force may be controlled to an appropriate value or the engagement force may be differentiated stepwise or continuously for every appropriate position.

When an open region of one hole 21a is larger than a substantial engagement area of the hook member, restraint effect of the engagement force cannot be attained readily, accordingly, an open region of one hole is designed so as to be smaller than a substantial engagement surface of the hook member of the fastening tape.

As a shape of the hole 21a, other than a circular hole shown in FIG. 6, as shown in FIGS. 8 and 9, a slit-like slender hole may be formed that has a predetermined width and is disposed along a width direction or a longitudinal direction of a sheet. A shape of the hole is not restricted particularly and though not shown in the illustrated example, a triangular hole may be formed and all holes are not necessarily identical.

In the illustrated example, in order to describe a configuration of the loop member sheet, for descriptive purpose, holes or slit holes having the same shape and size are regularly arranged. However, in case from a center in a width direction toward both side portions, the engagement force is varied stepwise or continuously for individual zones, from the center in the width direction toward the edge portion, sequentially, circular holes different in an open area are disposed, the disposition density of the circular holes having an identical open area is differentiated, and a distance of a slit width or a distance between slits is appropriately designed.

On the other hand, the holes 21a, 21a, from the viewpoint of their usage in an engagement section, may well be controlled so as to have an area in the range of substantially 30 to 80% as a total open region (total area including open regions of all holes) relative to an entire area of the loop member sheet 2. In this case, when each hole is circular, substantially 200 holes each having a diameter of 5 mm$\phi$ may well be disposed per 80 cm$^2$ and when a slit has a width of 1 to 5 mm, the slits may well be disposed at a pitch of substantially 2 to 5 times a slit width. At this extent, restraint of the engagement force can be sufficiently achieved and preferable strength can be developed.

Furthermore, in a range to an extent where the separation strength off the loop base sheet 20 is lowered by 10 to 50%, an arrangement mode of holes is suitably designed. The invention, without necessarily restricting to this range of numerical value, may be appropriately changed depending on the application.

When the loop base sheet 20 and the perforated cover sheet 21 are bonded, depending on the respective sheet materials, an adhesive selected from known adhesives 22 can be used. Such adhesive is suitable that does not become hard after bonding. In the present invention, it is undesirable to increase stiffness due to fusing of a loop base caused by heating, accordingly, thermal fusion is not preferable. In spite of this, even in the thermal fusion, the stiffness is not increased so much when dot emboss where an area of one dot is 5 mm$^2$ or less and an embossing rate is 10% or less or line emboss where a line width is 1 mm or less and adjacent lines are separated by 3 mm or more, accordingly, such thermal fusion can be used. Bonding due to a hot-melt adhesive is preferable for bonding sheet materials such as a nonwoven fabric or the like. A hot-melt bonded portion, with hardly hardening a bonded portion, may bond the sheet material. In particular, out of the hot-melt adhesives, an adhesive is preferable where care is taken so that the flexibility of a nonwoven fabric used in absorbent articles and sanitary articles may not be damaged.

Herein, when both sheet materials 20, 21 are bonded, an adhesive may be coated on a loop base sheet side or may be coated on a perforated cover sheet side. An adhesive, if required, may well be coated on an appropriate side and laminated for bonding. It is easier to produce by coating on the perforated cover sheet 21 than by coating an adhesive on the loop base sheet other than the arrangement pattern of holes.

In coating an adhesive, the adhesive may be coated on an entire surface of either one of the loop base sheet 20 and perforated cover sheet 21, or coated on a part of the surface in lines or in spots. Furthermore, by use of a coating machine such as a slot coater or the like an adhesive may be coated directly on a sheet material. Alternatively, hot-melt powder may be scattered, or a spray nozzle may be used to scatter the adhesive for coating. The coating is not particularly restricted.

By contrast, in the loop member sheet 2 of the present invention, by imparting the elasticity to the perforated cover sheet 21, the respective holes are formed scalable due to this elasticity. As such elastic sheet, there can be listed, for example, an elastic nonwoven fabric that makes use of engagement between fibers and a woven fabric provided with the elasticity owing to knitting. In making holes scalable due to elasticity, for the engagement of the holes with the hook members, the holes are expanded to allow engaging, and, after the engagement, due to contraction of the holes, unnecessary exposure of the loop can be decreased.

On the other hand, in the loop member sheet 2 of the present invention, an elastic material with resilience (not shown in the drawing) such as rubber thread, an elastomer sheet, a urethane sheet, other elastic sheet with resilience or the like is disposed between a loop base sheet 20 and a perforated cover sheet 21 which enables to impart the elasticity to the loop member sheet 2. Thereby, when the elasticity is imparted by use of an elastic member in this way, the holes 21a, 21a are hidden between wrinkles caused by the contraction of the loop member sheet 2, and the holes 21a and 21a are conspicuously exposed when the loop member sheet 2 is stretched. When the holes 21a and 21a are exposed for the engagement, a stretched state of a loop member sheet X2 is cancelled to enable to hide the holes 21a and 21a unnecessary for engagement again between wrinkles. Thus, in this way, unintended engagement can be decreased.

The bonding between the elastic member with resilience and the respective sheets can be appropriately selected. Similarly to the above bonding between the loop base sheet and perforated cover sheet, a hot-melt adhesive is preferably used.

Fifth Embodiment

Though not shown in the drawing, in a fifth embodiment of the present invention, a loop member is disposed on a back sheet and a perforated cover sheet is disposed so as to cover the loop member. In this embodiment, in the engagement section of the second embodiment, in order to control the engagement force of the engagement section as a whole, or in order to achieve partial difference of the engagement force of the engagement section, the perforated cover sheet described in the fourth embodiment is adopted.

Since a fundamental configuration of a diaper is similar to that of the second embodiment and a perforated cover sheet is similar to that of the fourth embodiment, descriptions thereof are omitted.

A unique configuration of the embodiment can be exemplified in the following. Since a back sheet is covered, at a range including a loop member, with a perforated cover sheet, the loop member is formed not only in an engagement section but also in a range larger than that. For example, in an entirety of a back sheet and a portion which does not require loop member can be covered with a portion of the perforated cover where the holes are not disposed. Thus, the engagement section can be appropriately formed. The bonding between the back sheet and perforated cover sheet is applied according to the bonding between the loop base sheet and perforated cover sheet, which is described in the fifth embodiment. The disposition of the elastic member with resilience and the like can be also performed according to the fifth embodiment.

Sixth Embodiment

In the next place, a sixth embodiment will be described. In an engagement section, in order to increase the engagement force or as means for forming partial difference of the separation strength in the engagement section, a process of opening holes penetrating through a back sheet is applied to form many openings.

FIG. 11(A) shows an example where, in a predetermined range set as an engagement region of a back sheet that constitutes an engagement section of the second embodiment, many penetrating openings 30, 30 . . . are disposed.

As obvious from the drawing, when many openings 30, 30 . . . are disposed in an engagement section X1, hook elements 40, 40 . . . of the hook member are engaged with the openings to improve the engagement force. In particular, even a nonwoven fabric or the like that has low basis weight and is less bulky provide sufficient engagement force. The engagement force with the fastening tape can be controlled by varying a formation ratio of the openings.

As a planar shape of the openings 30, 30 . . . in this case, there can be used a slit-like linear opening extended in a longitudinal direction of a diaper or in a width direction of a diaper or a roundish hole shape such as a circular, elliptic or comma-shaped shape. Furthermore, the arrangement thereof may be either regular or irregular and is optional over the engagement section. When it is used as means for partially forming difference of the separation strength in the engagement section, referring to the separation strengths of the respective portions, a hole-shape and disposition density are appropriately designed.

Furthermore, a sectional shape of the opening may be a shape where an edge of the opening may be flat to a surface of a diaper, or, as shown in FIG. 11(B), a shape erecting outwards of the diaper. When opening edges 30e, 30e . . . stand up even only slightly toward an external surface, a hook member is readily hooked for ensuring the engagement force.

From the viewpoint of securing appropriate engagement force with the hook member or of maintaining the strength of the nonwoven fabric, the openings are desirably formed at an aperture ratio of 30 to 80% with respect to an area ratio of the engagement section. When the aperture ratio is less than 30%, the hook elements that intrude into the openings are decreased so that sufficient engagement force cannot be obtained. On the other hand, when the aperture ratio exceeds 80%, the strength of the nonwoven fabric per se becomes weaker resulting in high risk of breaking.

Furthermore, when the opening is formed in slit, a slit width is set in the range of 0.2 to 5 mm and preferably in the range of 0.5 to 2 mm and a slit center distance is set in the range of 1 to 15 mm and preferably in the range of 5 to 10 mm. When the opening is formed in circular hole or the like, a diameter of one circle (maximum diameter) is set in the range of 0.5 to 10 mm and preferably in the range of 1.0 to 5 mm, and a center distance of holes is set in the range of 5 to 15 mm and preferably in the range of 7 to 10 mm. When the opening is formed in, other than circle, ellipse or comma shape, it is desirable that the size of such shape falls within a dimension of 5 mm×5 mm.

A technology for forming an opening according to the embodiment is applied to, without restricting to a predetermined range disposed as an engagement region of a back sheet, a loop member sheet having loop elements, a loop base sheet and a perforated cover sheet and may be adopted in the first through fifth embodiments as well. Accordingly, configurations, other than a configuration where openings are formed in an engagement section, such as a position, a range and a size of a face sheet, an absorbent body and an engagement section, and a configuration or the like of the fastening tape may be appropriately designed based on the first through fifth embodiments.

Other Embodiments

In the above embodiments, the separation strength becomes lower from a center portion in a width direction of a product toward edges on both sides. However, in the present invention, contrary to the above, an embodiment may be adopted where an engagement section is formed so that the separation strength of an engagement section may be higher from a center portion in a width direction of a product toward edges on both sides.

Furthermore, in the present invention, an embodiment may be adopted where an engagement section may be formed so that the separation strength may be higher or lower from one edge in a vertical direction of a product toward the other edge.

Still furthermore, in the present invention, an embodiment may be adopted where an engagement section is formed so that the separation strength may be higher or lower from a center portion in a width direction of a product toward edges on both sides and the separation strength may be higher or lower from one edge in a vertical direction of a product toward the other edge.

In the embodiments, when an engagement section is formed, which is partially different in the engagement force with the hook member, an appropriate design change may well be applied based on descriptions of the above embodiments 1 to 6.

Industrial Applicability

The present invention mentioned above may be used as well in, other than a disposable diaper that uses a hook and loop fastener mechanism, disposable articles such as an operating gown, a packaging material or the like that uses a hook and loop fastener mechanism.

DESCRIPTION OF REFERENCE NUMERALS

Figure 1:
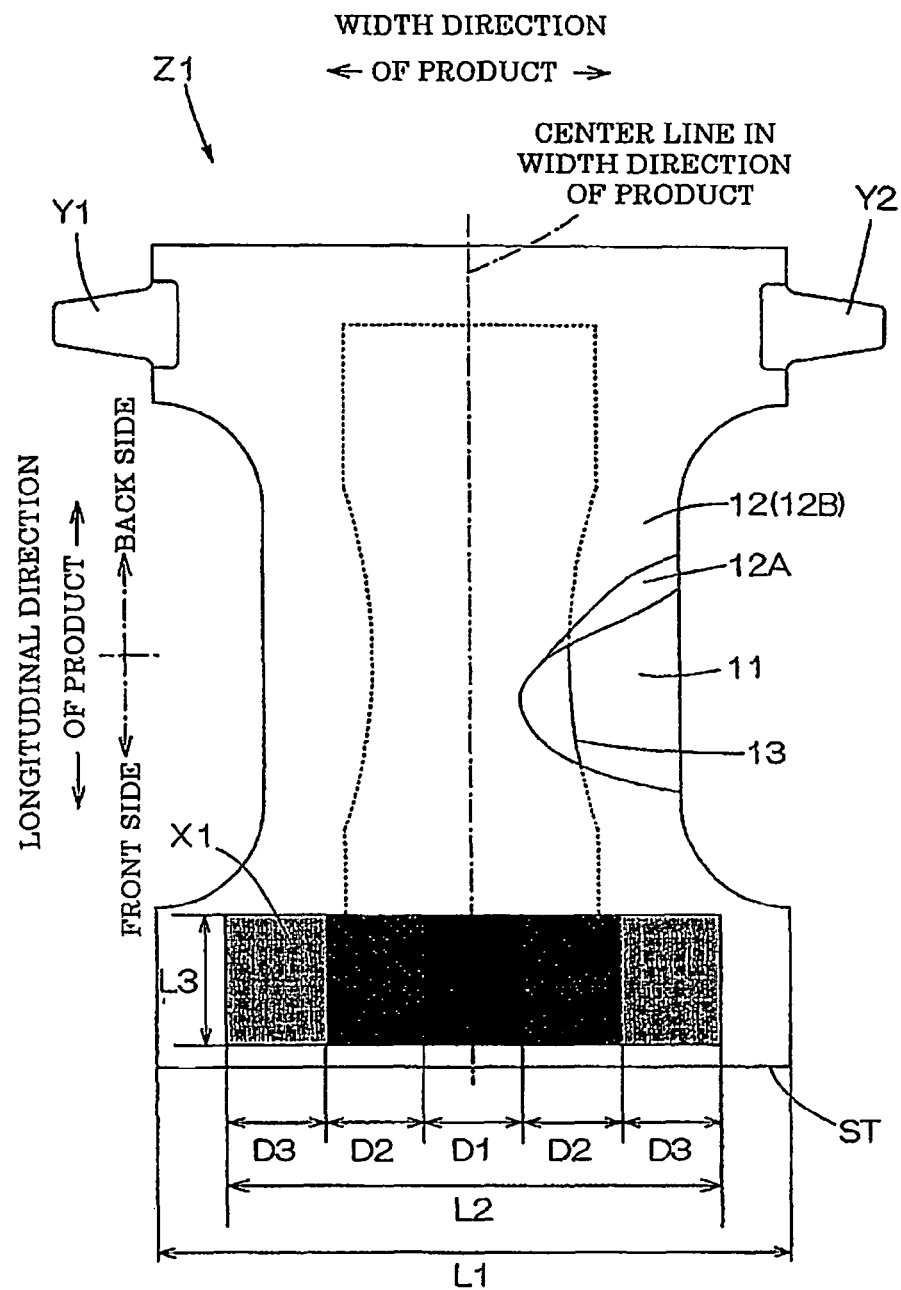
FIG. 1 is a development view of a first embodiment showing a fastening tape type disposable diaper according to the present invention.
Figure 2:
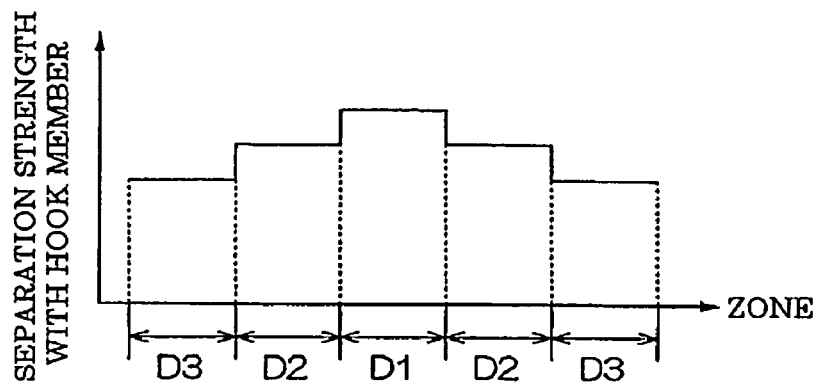
FIG. 2 is a view for explaining stepwise difference of the separation strength.
Figure 3:
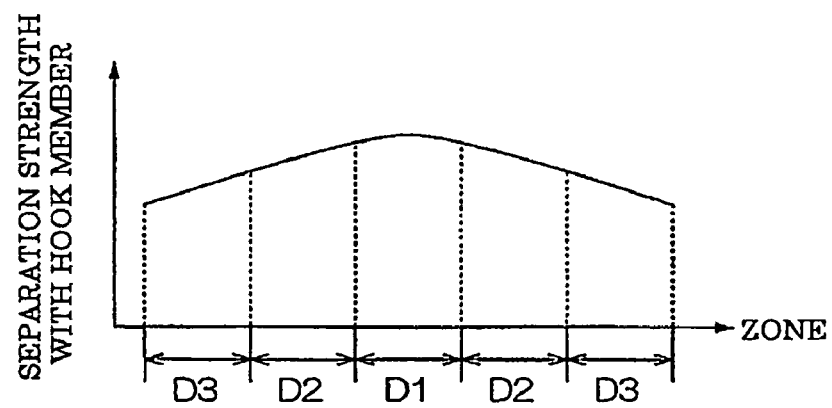
FIG. 3 is a view for explaining a case where the separation strength varies continuously.
Figure 4:
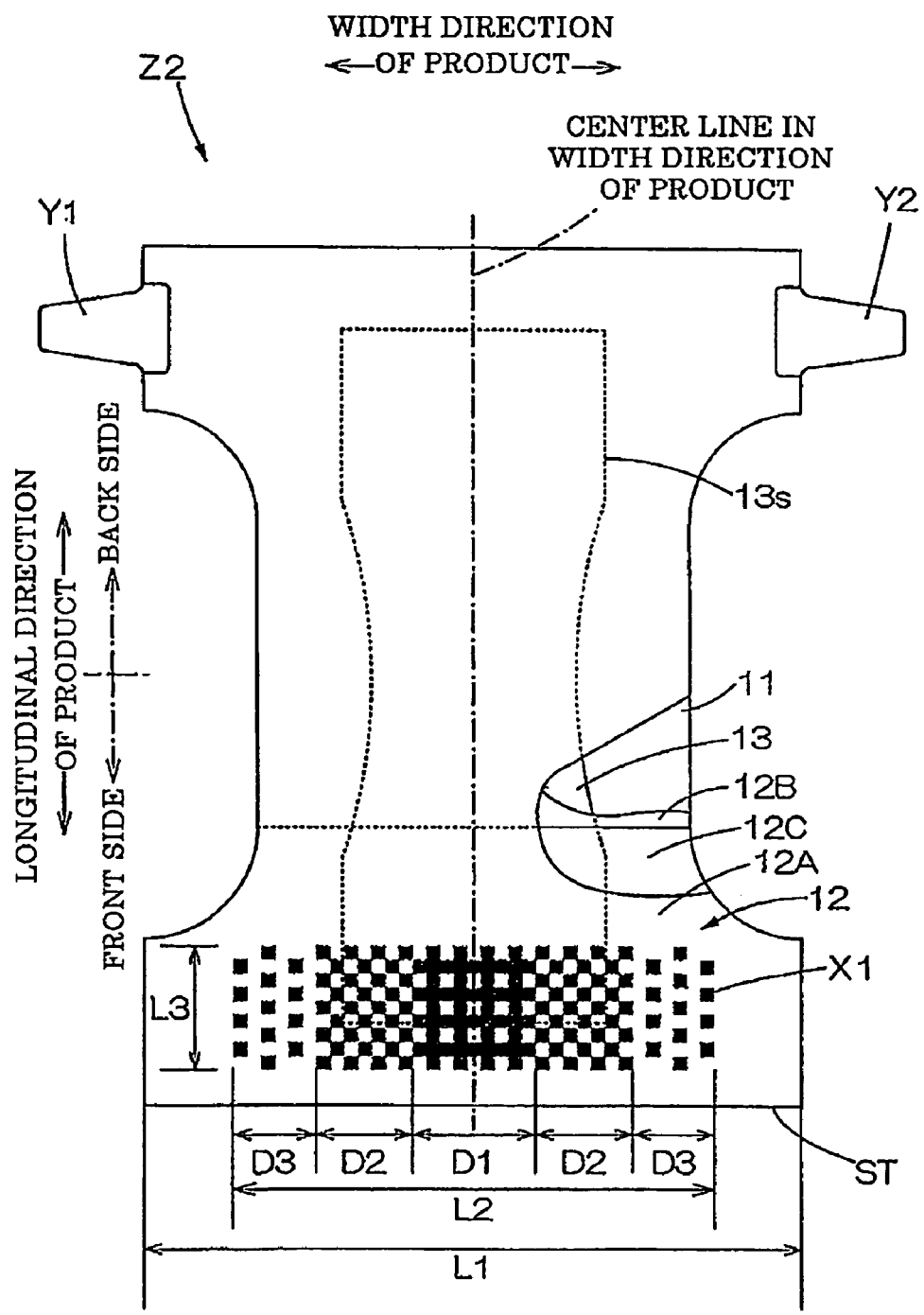
FIG. 4 is a plan view of a disposable diaper of a second embodiment.
Figure 5:
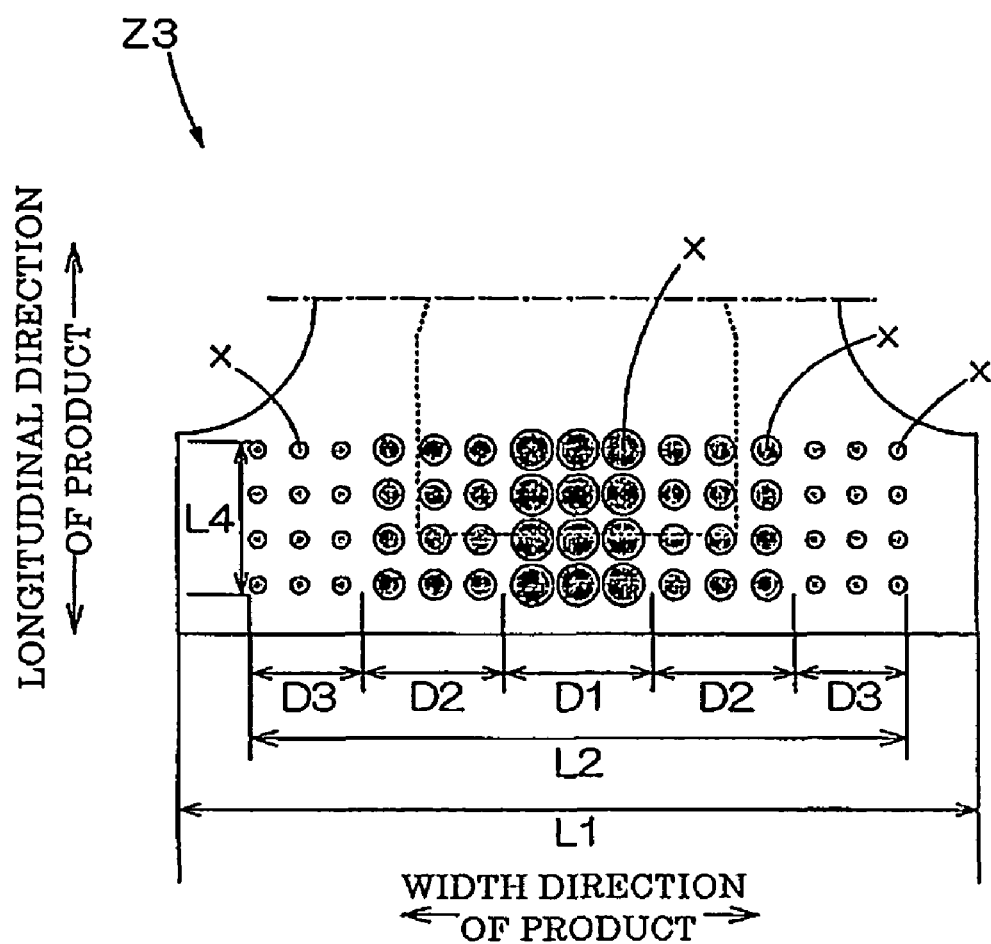
FIG. 5 is a plan view of a disposable diaper of a third embodiment.
Figure 6:
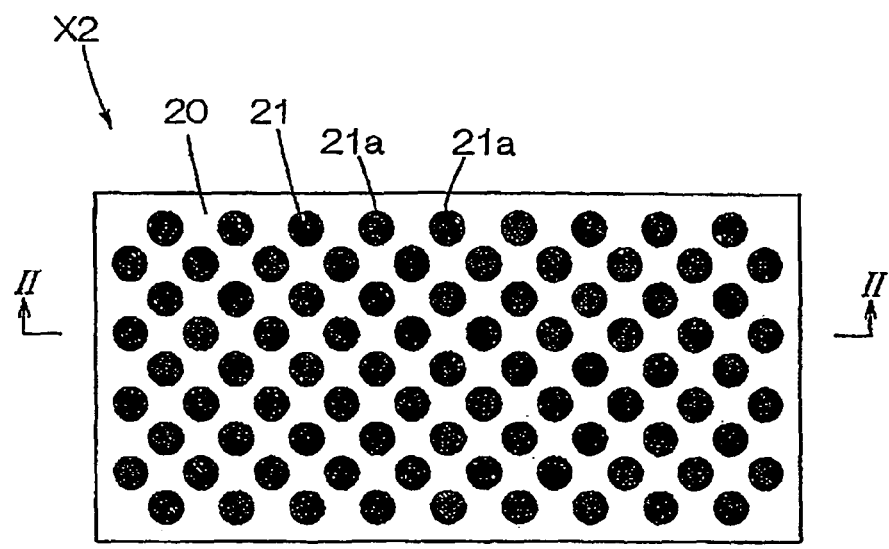
FIG. 6 is a schematic diagram showing the first embodiment of a loop member sheet of a hook and loop fastener according to the present invention.
Figure 7:
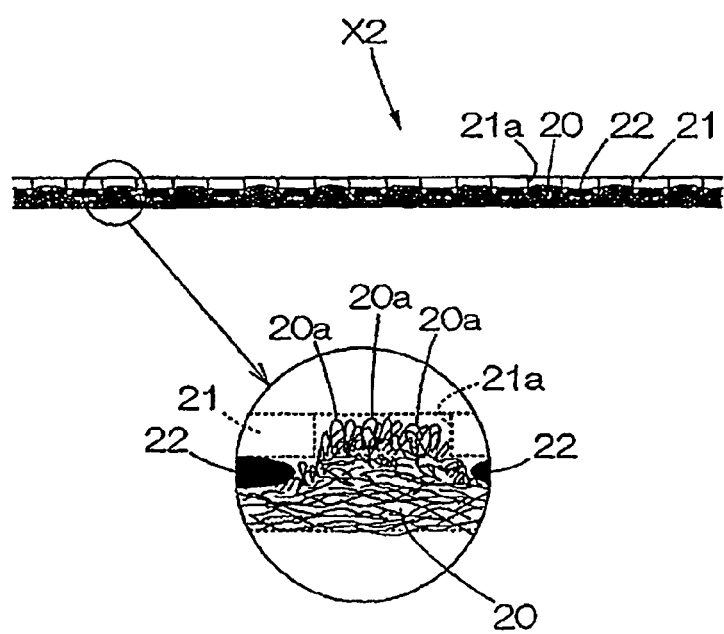
FIG. 7 is a II-II sectional view thereof.
Figure 8:
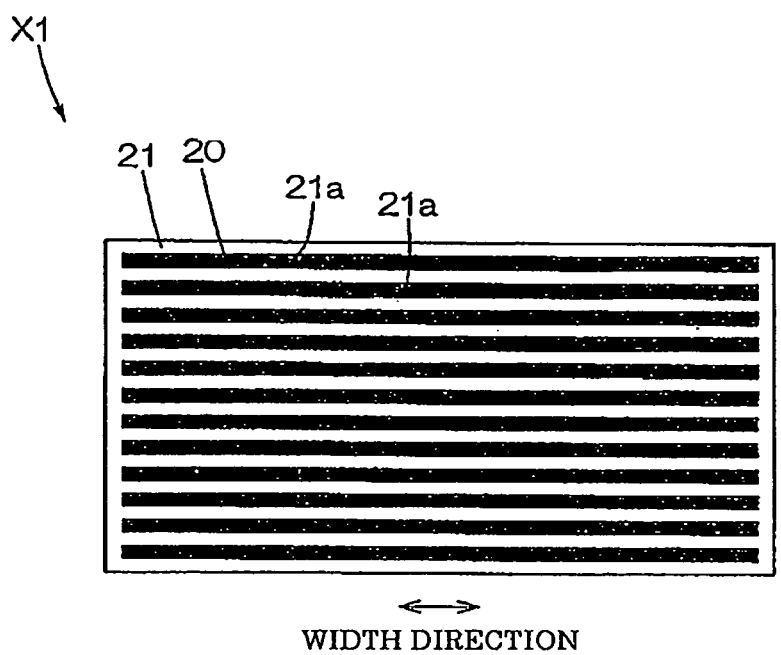
FIG. 8 is a schematic diagram showing the second embodiment of a loop member sheet of a hook and loop fastener according to the present invention.
Figure 9:
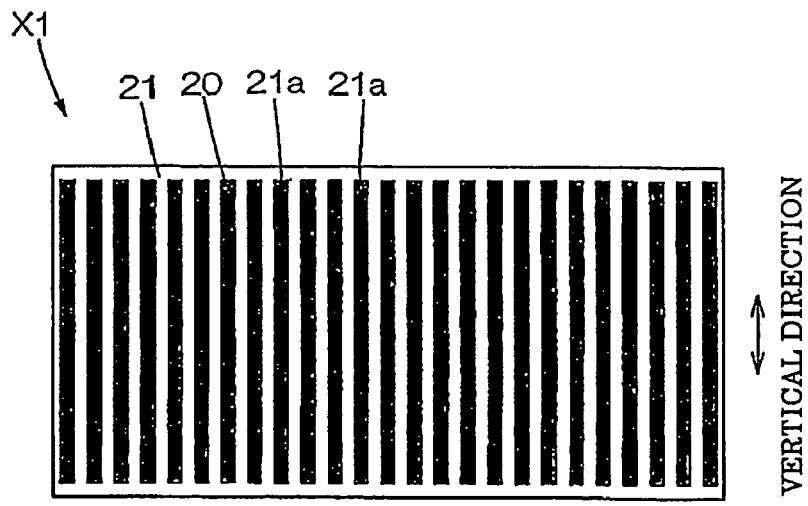
FIG. 9 is a schematic diagram showing the third embodiment of a loop member sheet of a hook and loop fastener according to the present invention.
Figure 10:
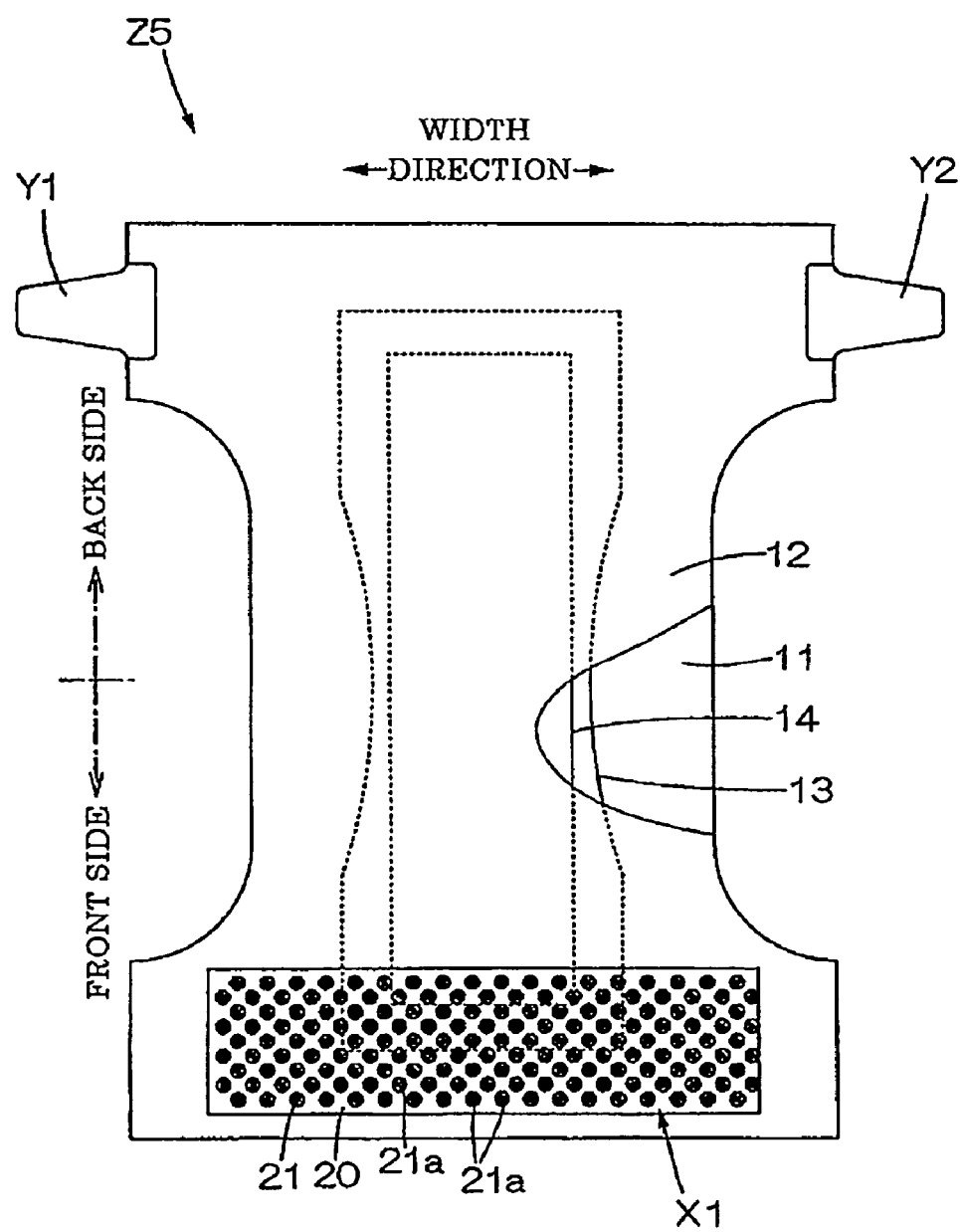
FIG. 10 is a development diagram of a fastening type paper diaper where a hook and loop fastener according to the present invention is adopted.
Figure 11:
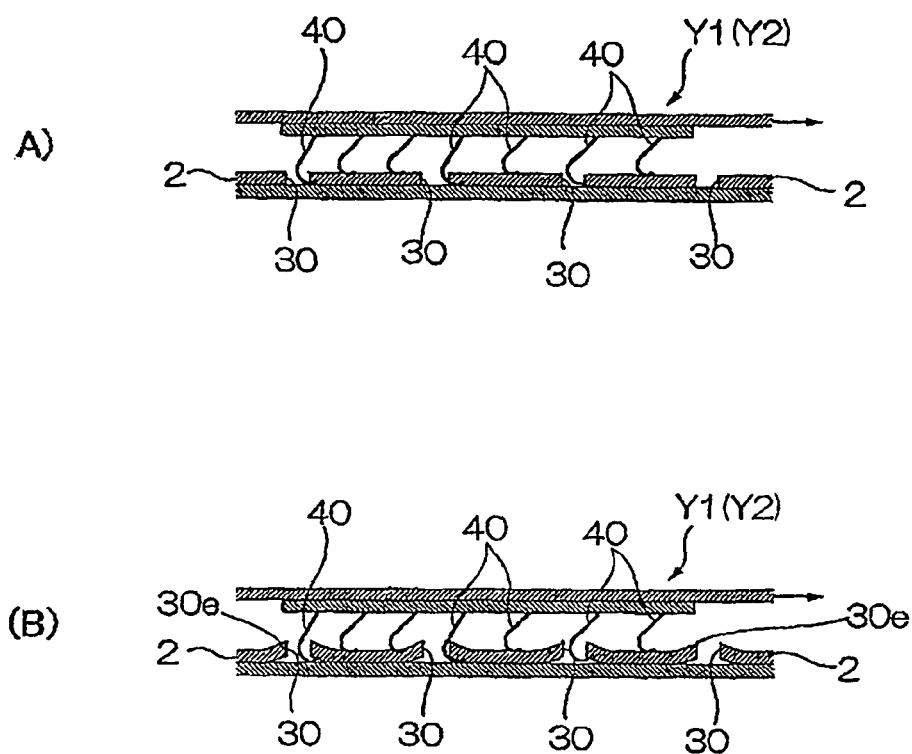
FIG. 11 is a plan view of a disposable diaper of a sixth embodiment.

X1 engagement section
X2 loop member sheet (engagement section formed from loop member sheet)
Y1, Y2 fastening tape
Z1, Z2, Z3, Z5 disposable diaper
11 face sheet
12 back sheet
12A liquid impervious film sheet
12B, 12C nonwoven sheet
E emboss
ST front side longitudinal direction edge
Z paper diaper
20a loop element
20 loop base sheet
21 perforated cover sheet
21a hole
22 hot-melt bonding section
14 second sheet

The invention claimed is:

1. An open type disposable diaper that includes: a liquid pervious face sheet; a liquid impervious back sheet; and an absorbent body disposed therebetween, wherein fastening tapes are disposed at edges of both sides of either one of a back side or a front side, the fastening tape is partially or entirely formed of a hook member of a hook and loop fastener, and the hook member is engaged with an engagement section disposed between edges of both sides of a front side or a back side for wearing, characterized in that
the engagement section is disposed so as to extend from a center in a width direction of a product toward edges on both sides and the separation strength off the hook member is constituted so as to be different stepwise or continuously from a center portion in a width direction of a product towards edges of both sides and/or from one edge in a vertical direction of a product towards the other edge, wherein the engagement section is:
a loop sheet having a configuration where, on a loop element-forming surface of a loop base sheet on which many loop elements are formed, a perforated cover sheet having a plurality of holes is stacked and bonded to engage with a hook member through the loop element-forming surface exposed from the holes of the perforated cover sheet or
a portion that is configured so that a range containing a loop member on which many loop elements formed by a fiber of a back sheet per se are formed is covered with a perforated cover sheet having a plurality of holes and, through the loop element-forming surface exposed from the holes, is engaged with the hook member.

2. The disposable diaper according to claim 1, wherein the perforated cover sheet is bonded, through a hot-melt adhesive, to a loop base sheet or a back sheet.

3. The disposable diaper according to claim 1, wherein the perforated cover sheet has the elasticity and is partially bonded to the loop base sheet or the back sheet and the respective holes are constituted scalably due to expansion and contraction of the perforated cover sheet.

4. The disposable diaper according to claim 1, wherein between the perforated cover sheet and the loop base sheet or between the perforated cover sheet and the back sheet, an elastic material with resilience is disposed.

5. The disposable diaper according to claim 1, wherein the perforated cover sheet is provided with many loop elements for engaging with the hook member formed on an external surface side of the diaper.

6. The disposable diaper according to claim 1, wherein, in at least one of predetermined ranges set as an engagement region of the loop member sheet, the loop base sheet, the perforated cover sheet and the back sheet, all of which have loop elements, many penetrating openings are disposed.

7. The disposable diaper according to claim 6, wherein the opening is formed by applying an opening operation from a side of a surface that is an internal surface side of the diaper to a side of a surface that is an external surface side of the diaper and an opening edge stands up outwardly.

* * * * *